(12) United States Patent
Shanov et al.

(10) Patent No.: US 11,730,857 B2
(45) Date of Patent: Aug. 22, 2023

(54) MAGNESIUM SINGLE CRYSTAL FOR BIOMEDICAL APPLICATIONS AND METHODS OF MAKING SAME

(71) Applicant: University of Cincinnati, Cincinnati, OH (US)

(72) Inventors: Vesselin N. Shanov, Cincinnati, OH (US); Vibhor Chaswal, Cincinnati, OH (US); Pravahan Salunke, Cincinnati, OH (US); Madhura Joshi, Cincinnati, OH (US); Guangqi Zhang, Cincinnati, OH (US); Mark J. Schulz, West Chester, OH (US); Sergey N. Yarmolenko, Chapel Hill, NC (US); Doug Nienaber, Loveland, OH (US)

(73) Assignee: University of Cincinnati, Cincinnati, OH (US)

( * ) Notice: Subject to any disclaimer, the term of this patent is extended or adjusted under 35 U.S.C. 154(b) by 61 days.

(21) Appl. No.: 17/195,997

(22) Filed: Mar. 9, 2021

(65) Prior Publication Data

US 2021/0196854 A1    Jul. 1, 2021

Related U.S. Application Data

(62) Division of application No. 15/504,767, filed as application No. PCT/US2015/045671 on Aug. 18, 2015, now abandoned.

(Continued)

(51) Int. Cl.
*C30B 11/00* (2006.01)
*C30B 15/00* (2006.01)
(Continued)

(52) U.S. Cl.
CPC ............ *A61L 27/047* (2013.01); *A61B 17/80* (2013.01); *A61B 17/86* (2013.01); *A61F 2/3099* (2013.01);
(Continued)

(58) Field of Classification Search
CPC ........ C30B 11/00; C30B 15/00; C30B 15/005
See application file for complete search history.

(56) References Cited

U.S. PATENT DOCUMENTS 2,029,898 A    2/1936 Schmidt et al.
2,149,076 A    2/1939 Stockbarger
(Continued)

FOREIGN PATENT DOCUMENTS

WO    2012075311 A2    6/2012

OTHER PUBLICATIONS

Burke, E.C., et al., "Plastic Deformation of Magnesium Single Crystals," Journal of Metals, vol. 4, Mar. 1952, pp. 295-303 (9 pages).

(Continued)

*Primary Examiner* — Nicholas W Woodall
(74) *Attorney, Agent, or Firm* — Wood Herron & Evans LLP

(57) ABSTRACT

A biomedical implant (16, 18) is formed from magnesium (Mg) single crystal (10). The biomedical implant (16, 18) may be biodegradable. The biomedical implant (16, 18) may be post treated to control the mechanical properties and/or corrosion rate thereof said Mg single crystal (10) without changing the chemical composition thereof. A method of making a Mg single crystal (10) for biomedical applications includes filling a single crucible (12) with more than one chamber with polycrystalline Mg, melting at least a portion of said polycrystalline Mg, and forming more than one Mg single crystal (10) using directional solidification.

11 Claims, 1 Drawing Sheet

Related U.S. Application Data

(60) Provisional application No. 62/038,407, filed on Aug. 18, 2014.

(51) Int. Cl.

| | | |
|---|---|---|
| *A61L 27/04* | (2006.01) | |
| *A61L 27/50* | (2006.01) | |
| *A61L 31/02* | (2006.01) | |
| *A61L 31/14* | (2006.01) | |
| *A61B 17/80* | (2006.01) | |
| *A61B 17/86* | (2006.01) | |
| *C30B 29/02* | (2006.01) | |
| *C30B 13/00* | (2006.01) | |
| *A61L 27/58* | (2006.01) | |
| *C30B 25/00* | (2006.01) | |
| *C30B 23/00* | (2006.01) | |
| *A61F 2/30* | (2006.01) | |
| *C25D 11/30* | (2006.01) | |
| *C30B 11/02* | (2006.01) | |
| *C30B 33/00* | (2006.01) | |
| *A61B 17/00* | (2006.01) | |
| *A61F 2/08* | (2006.01) | |

(52) U.S. Cl.
CPC ............ *A61L 27/58* (2013.01); *A61L 31/02* (2013.01); *A61L 31/022* (2013.01); *A61L 31/148* (2013.01); *C25D 11/30* (2013.01); *C30B 11/00* (2013.01); *C30B 11/02* (2013.01); *C30B 13/00* (2013.01); *C30B 15/00* (2013.01); *C30B 23/00* (2013.01); *C30B 25/00* (2013.01); *C30B 29/02* (2013.01); *C30B 33/005* (2013.01); *A61B 2017/00526* (2013.01); *A61F 2002/0858* (2013.01)

(56) References Cited

U.S. PATENT DOCUMENTS

| | | | | |
|---|---|---|---|---|
| 3,629,136 | A * | 12/1971 | Gobat | H01S 3/16 |
| | | | | 252/301.4 F |
| 3,687,135 | A | 8/1972 | Stroganov et al. | |
| 3,964,942 | A | 6/1976 | Berkenblit et al. | |
| 4,032,390 | A * | 6/1977 | Rice | C30B 29/60 |
| | | | | 117/25 |
| 4,076,574 | A * | 2/1978 | Pastor | C30B 29/12 |
| | | | | 117/76 |
| 4,142,031 | A | 2/1979 | Kato et al. | |
| 5,107,126 | A | 4/1992 | Yano | |
| 5,161,602 | A * | 11/1992 | Chang | C30B 11/002 |
| | | | | 164/122.2 |
| 6,969,502 | B2 | 11/2005 | Wehrhan et al. | |
| 8,202,477 | B2 | 6/2012 | Papirov et al. | |
| 8,222,153 | B2 | 7/2012 | Lienhart et al. | |
| 8,840,736 | B2 | 9/2014 | Harder et al. | |
| 8,888,841 | B2 | 11/2014 | Pandelidis et al. | |
| 8,888,842 | B2 | 11/2014 | Gulcher | |
| 8,906,293 | B2 | 12/2014 | Mukai et al. | |
| 8,956,403 | B2 | 2/2015 | Gregorich et al. | |
| 9,574,259 | B2 | 2/2017 | Miura | |
| 2003/0079675 | A1 * | 5/2003 | Lan | C30B 11/00 |
| | | | | 117/51 |
| 2004/0206267 | A1 | 10/2004 | Sambasivan et al. | |
| 2005/0079088 | A1 | 4/2005 | Wirth et al. | |
| 2005/0211408 | A1 * | 9/2005 | Bullied | B22D 27/045 |
| | | | | 164/122.2 |
| 2009/0262763 | A1 * | 10/2009 | Pan | C01B 35/128 |
| | | | | 117/3 |
| 2010/0163141 | A1 | 7/2010 | Shoji et al. | |
| 2011/0319977 | A1 * | 12/2011 | Pandelidis | C22F 1/06 |
| | | | | 623/1.42 |
| 2013/0145899 | A1 | 6/2013 | Song et al. | |
| 2014/0074159 | A1 | 3/2014 | Khoury et al. | |
| 2014/0236155 | A1 * | 8/2014 | Neubert | A61B 17/846 |
| | | | | 419/30 |
| 2015/0064053 | A1 * | 3/2015 | Washio | C22F 1/006 |
| | | | | 420/405 |

OTHER PUBLICATIONS

"Crystal Structure" https://www.physics.rutgers.edu/grad/506/materials%20crystal%20structure.pdf, accessed on Jul. 2014 (23 pages).

Fras, E., et al., "Processing Microstructure of Investment Casting Turbine Blade NITAC In-Situ Composites," Journal of Materials Engineering and Performance, vol. 5(1), Feb. 1996, pp. 103-110 (8 pages).

International Bureau of WIPO, PCT/US2015/045671, International Preliminary Report on Patentability, dated Feb. 21, 2017 (10 pages).

International Bureau of WIPO, PCT/US2015/045671, International Search Report and Written Opinion, dated Dec. 16, 2015 (15 pages).

Juncheng, L., "Optimization of control parameters of CdZnTe ACRT-Bridgman single crystal growth," Science in China Ser. E Engineering & Materials Science, vol. 47, No. 6, 2004, pp. 725-740 (16 pages).

Kwadjo, R., et al., "Cyclic Hardening of Magnesium Single Crystals," ACTA Metallurgica, vol. 26, No. 7, Jan. 1978, pp. 1117-1132 (16 pages).

Labzin, V.A., et al., "The Growth of Monocrystals of Low-Melting Metals," Physics of Metals and Metallurgy (USSR), May 6, 1957, pp. 168-169 (4 pages).

Lan, C.W., "Recent progress of crystal growth modeling and growth control," Chemical Engineering Science, vol. 59, 2004, pp. 1437-1457 (21 pages).

Long, T.R., et al., "Single-Crystal Elastic Constants of Magnesium and Magnesium Alloys," ACTA Metallurgica, vol. 5, Apr. 1957, pp. 200-207 (8 pages).

Mifune, T., et al., "Electron Irradiation Hardening of Magnesium and Zinc Single Crystals at 4.2 K," Journal of Nuclear Materials, vol. 169, 1989, pp. 64-72 (9 pages).

Mochalov, M.D., "Procedure for Obtaining Single Crystals of Magnesium from the Melt," Journal of Technical Physics (USSR) Zurnal techniceskoj fiziki, Issue 6, 1936, pp. 605 (6 pages).

Nichols, James L., "Orientation and Temperature Effects on the Electrical Resistivity of High-Purity Magnesium," Journal of Applied Physics, vol. 26, No. 4, Apr. 1955, pp. 470-472 (3 pages).

Reed-Hill, R.E., et al., "The Crystallographic characteristics of fracture in magnesium single crystals," ACTA Metallurgica, vol. 5, Dec. 1957, pp. 728-737 (10 pages).

Rzychon, T., et al., "Microstructure characterization of deformed copper by XRD line broadening," Archives of Materials Science and Engineering, vol. 28, Issue 10, Oct. 2007, pp. 605-608 (4 pages).

Sillekens, Erinc, et al., "Applicability of existing magnesium alloys as biomedical implant materials," Magnesium Technology 2009, presented Feb. 15-19, 2009, San Francisco, CA, USA (Conference Code 76923, 209-214) Abstract Only. (2 pages).

Sonda, Paul., et al., "The feedback control of the vertical Bridgman crystal growth process by crucible rotation: two case studies," Computers & Chemical Engineering, vol. 29, 2005, pp. 887-896 (10 pages).

Staiger, Mark P., et al., "Magnesium and its allow as orthopedic biomaterials: A review," Biomaterials, vol. 27, 2006, pp. 1728-1734 (7 pages).

Szekely, F., et al., "Characterization of self-similar dislocation patterns by x-ray diffraction," Physical Review B, vol. 32, No. 5, Aug. 2000, pp. 3093-3098 (6 pages).

Tanaka, H., et al., "Enlargement effect of the crucible size on Bi/sub 2/Sr/sub 2/CaCu/sub 2/O/sub y/ single crystals grown by a modified vertical Bridgman method," IEEE 15, pp. 3133-3136, 2005 (4 pages).

Wu, Anhua, et al., "Bridgman growth of bismuth tellurite crystals," Bull. Mater. Sci., vol. 28, No. 6, Oct. 2005, pp. 561-564 (4 pages).

(56) References Cited

OTHER PUBLICATIONS

Office Action in U.S. Appl. No. 15/504,767, dated Oct. 3, 2019, 8 pgs.
Office Action in U.S. Appl. No. 15/504,767, dated Apr. 1, 2020, 8 pgs.
Office Action in U.S. Appl. No. 15/504,767, dated Jul. 21, 2020, 8 pgs.
Office Action in U.S. Appl. No. 15/504,767, dated Nov. 12, 2020, 10 pgs.

* cited by examiner

MAGNESIUM SINGLE CRYSTAL FOR BIOMEDICAL APPLICATIONS AND METHODS OF MAKING SAME

CROSS-REFERENCE TO RELATED APPLICATIONS

This application is a divisional of U.S. patent application Ser. No. 15/504,767, filed Feb. 17, 2017, which is a U.S. national phase filing under 35 U.S.C. § 371 of International Patent Application No. PCT/US2015/045671, filed Aug. 18, 2015, which claims priority to claims the benefit of U.S. Provisional Application No. 62/038,407, filed Aug. 18, 2014, the disclosures of which are incorporated by reference herein in their entireties.

STATEMENT REGARDING FEDERALLY SPONSORED RESEARCH

This invention was made with government support under 0812348 awarded by National Science Foundation. The government has certain rights in the invention.

TECHNICAL FIELD

The present invention relates generally to compositions and methods for making magnesium single crystal and, more specifically, to compositions and methods for making magnesium single crystal for biomedical applications.

BACKGROUND

Metallic materials continue to play an essential role as biomaterials to assist with the repair or replacement of bone tissue that has become diseased or damaged. Metals are more suitable for load-bearing applications compared with ceramics or polymeric materials due to their combination of high mechanical strength and fracture toughness. Currently, commonly used metallic biomaterials include stainless steels, titanium, and cobalt-chromium-based alloys. A limitation of these current metallic biomaterials is the possible release of toxic metallic ions and/or particles through corrosion or wear processes leading to inflammatory cascades, which reduce biocompatibility and cause tissue loss. Moreover, the elastic moduli of current metallic biomaterials are not well matched with that of natural bone tissue, resulting in stress shielding effects that can lead to reduced stimulation of new bone growth, which decreases implant stability. Current metallic biomaterials are essentially neutral in vivo, remaining as permanent fixtures. In the case of plates, screws, and pins used to secure serious fractures, the implant may have to be removed by a second surgical procedure after the tissue and bone have healed sufficiently. Repeated surgeries increases costs to the health care system and further morbidity to the patient.

Magnesium is a lightweight material as compared to conventional metallic biomaterials such as aluminum and steel. Further, the fracture toughness of magnesium is greater than conventional ceramic biomaterials. Thus, magnesium and its alloys have been applied as lightweight, degradable, load bearing orthopedic implants. However, the use of such implants is limited by factors such as corrosion resistance and the need for a non-toxic, biologically compatible material. Particularly, some magnesium alloys contain bio-toxic elements, such as aluminum, and rare earth metals, which are employed to improve mechanical and corrosion properties. These elements may migrate from the Mg implants into the blood stream and cause cytotoxicity.

Accordingly, improved compositions and methods of making materials useful in biomedical applications are needed to address the shortcomings of existing methods and biomaterials.

SUMMARY

In its broadest aspects, embodiments of the present invention are directed to a biomedical implant made of high purity magnesium (Mg) single crystal and methods of making such a biomedical implant. Biomedical implants according to embodiments of the present invention may be biodegradable. In one embodiment, a biomedical implant made of a Mg single crystal is post treated to control the mechanical properties and/or corrosion rate of said Mg single crystal without changing the chemical composition thereof. In one embodiment, a method of making a Mg single crystal for biomedical applications includes filling a single crucible with more than one chamber with polycrystalline Mg, melting at least a portion of said polycrystalline magnesium, and forming more than one Mg single crystal using directional solidification.

In one embodiment, a method of making a Mg single crystal for biomedical applications includes filling a single crucible designed with a desired shape with polycrystalline magnesium, melting at least a portion of said polycrystalline magnesium, and forming a single crystal based on the shape of the crucible.

In one embodiment, a method of making a Mg single crystal for biomedical applications includes filling a two-part, or split mold, crucible and locked with carbon nanotube (CNT) thread or CNT sheet, with polycrystalline magnesium, melting at least a portion of said polycrystalline magnesium, and forming a single crystal thus enabling easy release of the grown crystal.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

As compared to polycrystalline magnesium, Mg single crystals generally have: no grain boundaries; high strength; high purity (e.g., 99.998%); and high corrosion resistance. The higher the purity of magnesium, the lower the corrosion rate is. Advantageously, the mechanical properties of pure Mg single crystal are similar to those of a human bone. Additionally, the elongation of a pure Mg single crystal is much greater compared to, for example, a polycrystalline AZ magnesium alloy (e.g., AZ91; AZ61; AZ31). The greater elongation allows great ductility and enables impact absorption. The latter is important for creating medical implants that do not undergo catastrophic failures upon sudden stress or impact. Additionally, Mg single crystals exhibit "superplasticity." Superplasticity has traditionally been seen in ultra-fine grained materials. This property enables unprecedented metal ductility and toughness, which is highly desired for medical implants and prevents catastrophic failures when exposed to an impact.

Figure 1:
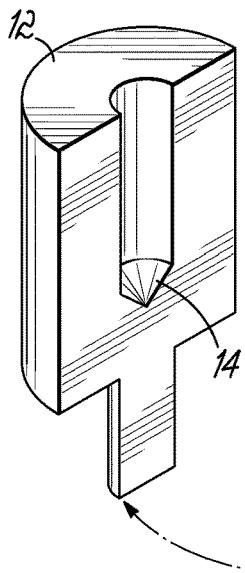
FIG. 1 is a perspective view of a Mg single crystal formed in a split mold crucible according to an embodiment of the present invention.
Figure 1A:
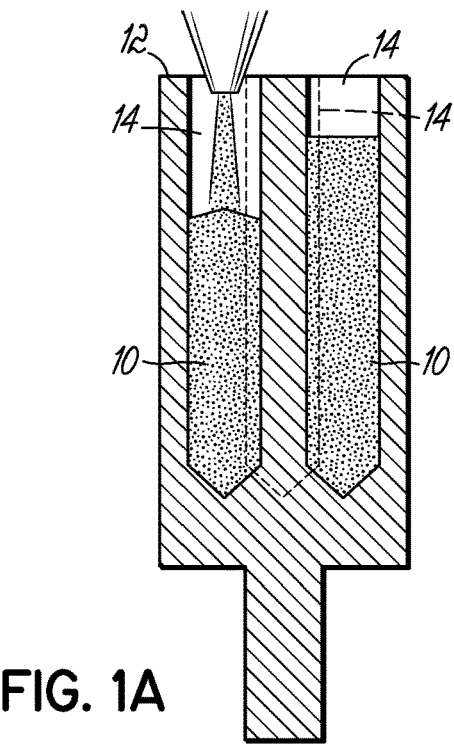
FIG. 1A is a cross-sectional view of the crucible being filled with a material.

Mg single crystals useful in embodiments of the present invention may be grown according to numerous methods. With reference to FIG. 1, and in one embodiment, a Mg single crystal 10 may be grown according to a directional solidification technique called the Bridgman-Stockbarger technique. This is a directional solidification process wherein the Mg single crystal is grown from a melt by utilizing an extremely slow rate of cooling. The charge, or raw magnesium, is contained in a closed container or crucible 12. The crucible 12 is heated in a furnace to melt the magnesium after which the crucible 12 is moved out of the hot zone furnace at a very slow speed. This gradual cooling allows for the nucleation of a single nucleus of solid magnesium. As the crucible 12 moves out of the hot zone, the interface between the solid nucleus and the melt advances further into the melt, eventually resulting in the entire melt solidifying into one single crystal 10. Using this process, the shape and size of the crystal 10 can be controlled. As discussed further below, a seed crystal with a desired orientation may be employed at the tapered end of the crucible to promote growth with a preset crystal orientation. The Bridgman-Stockbarger technique is generally faster and cheaper than other single crystal growth techniques. However, it should be recognized that Mg single crystals may be grown using alternative techniques. By way of example, Mg single crystals may be formed using the Czochralski method, the floating zone method, chemical vapor deposition, and physical vapor deposition, or any combination thereof.

In one embodiment, a Mg single crystal may be grown using a crystal grower including two furnaces with precise temperature control up to about 1200° C. and a computerized translation module. The computerized translation module provides programmable linear motion from, for example, about 0.5 mm/hrs to about 5 mm/hrs and a rotation speed from zero to about 15 rpm. In this manner, the module secures smooth travel of a crucible filled with high purity liquid magnesium. The crucible may have a variety of useful configurations and may be configured to grow the crystal in a desired shape. By way of example, the crucible may be rectangular, screw-shaped, or cylindrical. In one embodiment, the crucible stays in a high temperature zone of the furnace at a temperature of about 90° C. above the melting point of magnesium until the whole amount of magnesium melts. The process may include a soaking time, discussed further below. Next, the crucible is driven with a preset linear speed towards a low temperature zone, which is maintained slightly below the melting point of magnesium. The boundary between the high and low temperature zones forms a temperature gradient that drives the directional solidification starting at a conical end of the crucible. In such an embodiment, single crystals with sizes up to about 150 mm in length and about 20 mm in diameter can be obtained. The quality of the crystals may be controlled by varying the growth time, crucible rotation speed, temperature gradient, and crucible design. Additionally, the grown Mg single crystal may undergo annealing at temperatures below the magnesium melting point for 1 to 50 hr, for example. In one embodiment, a grown Mg single crystal undergoes annealing in argon at 645° C. for 14 hr. The annealing improves the quality of the crystal and reduces structural defects.

The soaking time is the period of time the melted magnesium is kept at a constant temperature above the melting point within the crucible before starting the directional solidification. In one embodiment, the soaking temperature may be about 10 to about 150° C. above the melting point. Soaking allows the magnesium melt to completely homogenize in terms of harmful temperature gradients or impurities. This procedure enables growing of Mg single crystal with superior quality. Generally, the longer the soaking time, the better the quality of the single crystal is. The soaking time may be, for example, 1 to 50 hr. In one embodiment, the soaking time may be about 30 hr. Using a soaking time of above 30 hr, the positive effect is not proportionally pronounced and increases to total fabrication time without substantial benefit.

In one aspect of the present invention, the design and dimensions of the crucible used to grow a Mg single crystal may be adjusted to allow for the growth of large single crystals with a preset form. Accordingly, the growth of the Mg single crystal may be successfully scaled up to meet the needs of the biomedical industry. In one embodiment, multiple Mg single crystals are grown in a single crucible. Mg single crystals may also be grown in a split mold crucible (shown in FIG. 1) wrapped with a carbon nanotube (CNT) thread or a CNT sheet, which allows for the easy release of the grown crystal from the crucible. The CNT wrap does not expand when heated, thus maintaining the crucible in the locked position.

In one embodiment, the Mg single crystal may be grown with a preset orientation. In the absence of a Mg seed single crystal, the Mg melt starts crystallizing within the tapered part of the crucible with an orientation close to (0001). With reference to FIG. 1, in order to avoid uncontrolled crystallographic orientation of the grown crystal, a Mg seed single crystal may be placed in the tapered part 14 of the crucible 10. The seed crystal can be cut of a Mg single crystal and polished and etched prior use. The disadvantage of using a Mg seed single crystal is that the melting point of magnesium is relatively low (i.e., 650° C.), meaning the risk of fully melting the expensive seed crystal is large. Accordingly, a seed crystal of a metal other than magnesium may be used. In one embodiment, a zirconium (Zr) seed crystal may be used for controlling the orientation of the Mg single crystal. Zirconium has a high melting point of about 1,855° C. and has negligible lattice mismatch with magnesium. Both metals reveal HCP crystal structure with lattice constants of a=0.323 nm and c=0.5148 nm for Zr and a=0.3209 nm and c=0.5209 nm for Mg.

In one embodiment, a polycrystalline magnesium article may be converted to a Mg single crystal article having the same shape. For example, a polycrystalline magnesium screw may be converted to a Mg single crystal screw. In one embodiment, a polycrystalline magnesium screw may be inserted in a graphite crucible by screwing. After performing directional solidification, the polycrystalline Mg screw is converted into a single crystal screw. In this regard, the internal shape of the crucible, when assembled, is an exact negative replica of the grown object (in this case a screw). The achieved result allows minimizing and even avoiding machining of the single crystal objects thus improving their quality. Additionally, or alternatively, the grown Mg single crystals can be machined or forged to achieve the desired shape and size.

In one aspect of the present invention, the Mg single crystal may undergo additional processing steps to improve the mechanical and corrosion properties. More specifically, the corrosion and mechanical properties of the Mg single crystal may be improved without changing the chemical composition thereof (e.g., by adding toxic alloying elements). The corrosion rate of pure Mg single crystals (e.g., 99.998%) may be controlled without changing the composition thereof by chemical etching and anodization. In one embodiment, etching of the Mg single crystal forms a nanometer thick and dense oxide film on the surface of the crystal, which varies with etching time. The film contributes to a better corrosion behavior in vitro and especially in vivo. Chemical etching may be conducted on the grown Mg single crystal for about 10 to about 100 seconds. In one embodiment, the Mg single crystal undergoes etching for about 30 seconds. Using such a treatment improves the properties of both polycrystalline and single crystal magnesium or its alloys in corrosion media used for biomedical testing, including in vitro and in vivo.

The mechanical properties of pure Mg single crystals may be controlled without changing the composition thereof by a variety of post-treatment methods. In one embodiment, a Mg single crystal may be irradiated using, for example, electron beam, gamma, or neutron irradiation. Electron irradiation of Mg single crystals causes the flow stress to proportionally increase with the square root of the electron dose due to irradiation-induced interstitials in the HCP metals.

In one embodiment, the mechanical properties, such as strength and toughness, of the Mg single crystal are changed without changing the composition thereof using controlled cold work (CW) induced hardening. Cold working involves plastic deformation of metals below the recrystallization temperature. Using uniaxial CW in a hydraulic press, for example, initially increases the strength of Mg single crystals. Cold work up to 13% may increase the strength of a Mg single crystal by 50%, for example. A maximum strength may be reached at about 15% CW according to Knoop micro-hardness measurements. In such an embodiment, higher CW would reduce the strength of Mg single crystals. If the single crystal needs to be strengthened in spite of favorable orientation, then the mechanical strength values may be increased by increasing the dislocation density. In one embodiment, the Mg single crystals may be fatigued in axial push-pull mode at constant plastic strain amplitude thus causing hardening of the crystal.

In one embodiment of the present invention, single crystals of magnesium alloys may be grown for use in biomedical applications. In other words, the starting material for growing the single crystal may be a magnesium alloy. Avoiding the segregation of the alloying elements during solidification may be achieved by varying the growth rate. Additionally, applying an annealing procedure to the grown crystal below the melting point enables redistribution of the alloying elements.

Figure 2:
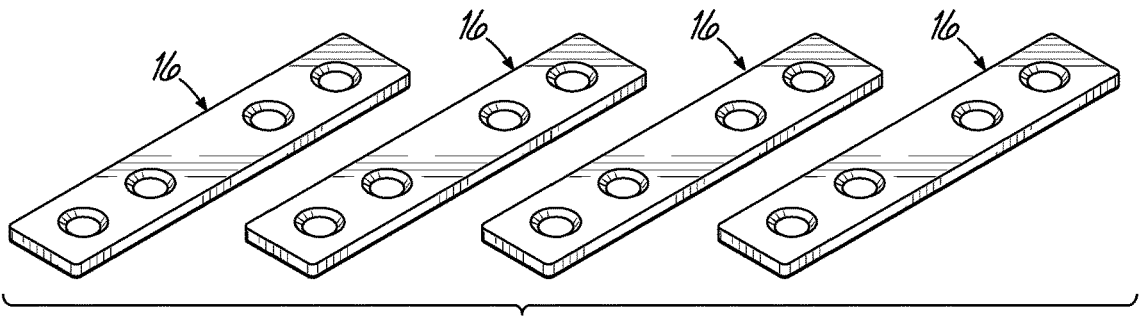
FIG. 2 is a perspective view of Mg single crystal bone plate implants according to an embodiment of the present invention.
Figure 3:
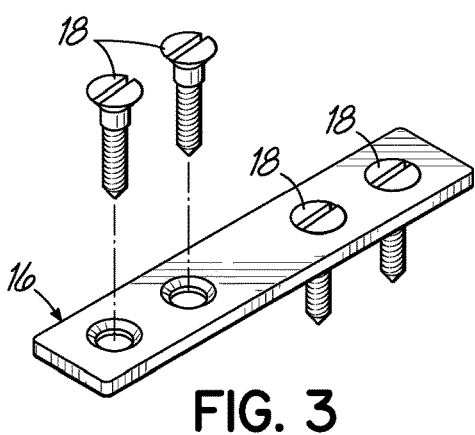
FIG. 3 is a perspective view of Mg single crystal screw implants and a Mg single crystal bone plate implant according to an embodiment of the present invention.

With reference to FIGS. 2 and 3, embodiments of the present invention may be used in a variety of biomedical applications. A non-limiting list of exemplary biomedical applications includes the use of Mg single crystals in anterior cruciate ligament (ACL) interference screws, temporomandibular joint (TMJ), temporomandibular devices, and bone fixation plates 16 and screws 18. These implants may be implanted in a mammal, such as a human. The higher ductility of Mg single crystals is useful for implants located in regions experiencing significant motion and interplay between bones and tissues such as an ACL ring and craniofacial devices. Additionally, the Mg single crystal material form having high purity and being free of grain boundaries provides a reduced corrosion rate and increased strength after appropriate surface treatment (e.g., mechanical-chemical polishing and/or anodization).

In order to facilitate a more complete understanding of the embodiments of the invention, the following non-limiting examples are provided.

Example 1

Polycrystalline magnesium with a purity of 99.95% from Alfa Aesar was used as a starting material. The magnesium was loaded in a graphite crucible and melted in a quartz tube surrounded by a 3 zone vertical furnace under Ar. Single crystal samples were prepared by the Bridgman technique in a multiple-zone Easy Crystal Furnace by CVD Equip. Corp. using the graphite crucible placed in a sealed quartz cylindrical housing to maintain a positive Ar atmosphere. As discussed above, the shape and size of the crystal is determined by the design of the graphite crucible. Two different sizes of graphite crucibles were used: one with a 6.5 mm bore size and another with a 8 mm bore size. The length of the two crucibles was 100 mm. Mg single crystals having a purity of 99.995% for screw devices were grown with a length of 65 mm and diameters 6.5 mm and 8 mm. These sizes allow for easy machining of the Mg single crystal to the final size.

Metallographic and x-ray diffraction characterization of the cast ingots was conducted to confirm single crystallinity. The single crystal rods were cut into discs for analysis. Cutting of the crystal required special tools such as traveling-wire Electrical Discharge Machining (EDM). To eliminate the defects after cutting or machining, a conventional electropolishing set-up and a stainless steel cathode were used. The electrolyte comprised three parts of 85% phosphoric acid and five parts of 95% ethanol both cooled to approximately 2° C. before mixing. More rapid electropolishing can be obtained by performing it at 4° C. in an electrolyte consisting of 10% hydrochloric acid and ethylene glycol monoethyl ether.

The x-ray diffraction characterization was accomplished using a Bruker Discover D8 having rotation along 4 axes ($\phi$, X, $\theta$, $2\theta$). Single crystallinity was confirmed by mapping the cast ingot using x-ray diffraction across the whole length, and combining the results with optical micrographs obtained after chemical etching of the polished surface. The appearance of x-ray peaks across the whole sample indicated the presence of the same crystal grain across the length. Optical microscopy confirmed that the grain was indeed a single crystal. The flat surface of the disc is along a pyramidal plane. In addition, the crystal rod axis is about 22° off the (002) basal plane. Finally, a Laue diffraction pattern from the Mg single crystal revealed a 6 fold symmetry low index zone which is indicative of (001) basal plane and of good HCP symmetry including absence of sub-grains or twinning defects.

An IZOD impact test of Mg single crystal and polycrystalline magnesium were conducted. For the Mg single crystal, all energy was absorbed by twinning in crack dampening and plastic deformation. The Mg single crystal sample bent but did not break despite the created notch prior the impact. The polycrystalline sample fractured near the notch, which indicates the possibility of catastrophic failure upon impact. Accordingly, more energy is needed to initiate crack propagation in a Mg single crystal.

Uniaxial compression tests were carried out using untreated Mg single crystal and polycrystalline magnesium. The polycrystalline samples showed higher strength, however the Mg single crystal revealed higher toughness. In other words, the polycrystalline magnesium is more rigid. In the single crystal, there are fewer barriers, such as grain boundaries, to the movement of dislocations, therefore it is easier to deform. Distinct shear zones at an angle to the direction of loading or compression in the single crystal were observed. This is indicative of one slip system or deformation twinning, which governs the plastic deformation.

Three-point bend tests were also carried out using untreated Mg single crystal and polycrystalline magnesium. The single crystal samples were more flexible and softer and required less loading to reach the same bending or displacement as the polycrystalline samples. The polycrystalline magnesium was stiffer and required more loading to bend. Neither sample fractured in this test.

Example 2

A single crystal was treated to around 15% CW and wire cut to fabricate a tensile sample. A tensile test carried out on CW sample showed high strength. The sample remained unbroken and did not reveal any permanent deformation at stresses higher than fracture stress of non-cold worked single crystals. This indicates that controlled CW improves the strength of Mg single crystals.

A new phenomenon for the Mg single crystal called "superplasticity" was discovered. High toughness and superplastic tendencies were revealed when tensile tests were conducted on non-cold worked samples. Despite their lower yield strength (e.g., about 60 MPa), they exhibit tendency for unusually high plastic deformation up to about 50% to about 60% indicating multiple twinning and slip induced inhibition of strain localization and potential superplastic tendencies. Samples exposed to CW showed increased strength and were not able to break in this experiment due to limitation of the load in the used tensile tester.

Single crystals both cold worked and as cast show high ductility. A polycrystalline specimen showed rough surface due to low ductility. As cast and cold worked, the single crystal samples showed similar fracture surfaces and the deformation in these samples may be due to one slip system or twinning. The Mg single crystal showed high ductility (superplasticity) of 60% due to about 20° off the (002) plane.

Example 3

Samples from polycrystalline magnesium and from grown pure Mg single crystal were cut using electrical discharge machining (EDM) wire machine into discs of having a diameter of 6.5 mm and a thickness of 2 mm. The discs were successively hand polished using the 600 grit and 1200 grit SC paper in isopropyl alcohol. After each polishing pass, the individual discs were sonicated in ethanol for two minutes and then air dried. After, the discs were chemical etched for 10 seconds. The chemical etchant used was made of nitric acid, methanol and ethanol (NME) in the ratio 1:2:1. After etching, the samples were immediately rinsed using ethanol and air dried. Such a treatment dramatically reduced the corrosion rate of the polycrystalline or monocrystalline magnesium discs in corrosion media used for biomedical testing, including in vitro and in vivo.

While all of the invention has been illustrated by a description of various embodiments and while these embodiments have been described in considerable detail, it is not the intention of the Applicants to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicants' general inventive concept.

What is claimed is:

1. A method of making a Mg single crystal for biomedical applications comprising:
    filling a single crucible including more than one chamber with polycrystalline Mg;
    melting at least a portion of said polycrystalline Mg;
    forming more than one Mg single crystal using directional solidification; and
    applying an annealing procedure in argon at a temperature maintained below the magnesium melting point for 1 to 50 hrs, thereby eliminating segregation of said Mg alloy during growth of said Mg single crystal.

2. The method of claim 1, wherein said polycrystalline Mg is a polycrystalline Mg alloy.

3. The method of claim 2, wherein the magnesium alloy contains rare earth elements.

4. The method according to claims 1, 2, or 3, wherein the controlled crystallization of said Mg crystallization is caused by directional solidification from the Mg melt utilizing at least one method chosen from the Czochralski method, the Bridgman method, and the floating zone method.

5. The method of claim 1, further comprising linear motion of the crucible of 0.5 mm/hr to 5 mm/hr and a crucible rotation rate of 0-15 rpm.

6. The method of claim 1, further comprising use of a single crystal of zirconium or magnesium as a seed crystal.

7. The method of claim 1, wherein the Mg single crystal is grown from a melt exposed to a soaking time of 1-50 hr and a constant soaking temperature of 10-150° C. above the melting point of magnesium.

8. The method of claim 7, wherein the Mg single crystal is grown from a melt exposed to a soaking time of 30 hr and a constant soaking temperature of 75° C. above the melting point of magnesium.

9. The method of claim 1, wherein the length to diameter ratio of the single crystals is in a range chosen from 7.5:1, 8.125:1, and 10:1.

10. The method of claim 1, wherein the annealing temperature is 645° C. and the annealing procedure is applied for 14 hrs.

11. A method of making a Mg single crystal for biomedical applications comprising:
    filling a split mold crucible locked with a carbon nanotube (CNT) thread or a CNT sheet with polycrystalline Mg;
    melting at least a portion of said polycrystalline Mg; and
    forming Mg single crystal using directional solidification.

* * * * *